(12) United States Patent
Helton et al.

(10) Patent No.: US 10,390,999 B2
(45) Date of Patent: Aug. 27, 2019

(54) METHOD AND APPARATUS FOR MANUFACTURING AN ABSORBENT ARTICLE INCLUDING A DISCRETE SUBSTRATE HAVING A RUGOSITY

(71) Applicant: The Procter & Gamble Company, Cincinnati, OH (US)

(72) Inventors: Ronald Herbert Helton, Cincinnati, OH (US); Darrell Ian Brown, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 636 days.

(21) Appl. No.: 14/724,028

(22) Filed: May 28, 2015

(65) Prior Publication Data

US 2015/0342791 A1 Dec. 3, 2015

Related U.S. Application Data

(60) Provisional application No. 62/004,240, filed on May 29, 2014.

(51) Int. Cl.
*A61F 13/15* (2006.01)
*B65H 45/16* (2006.01)
(Continued)

(52) U.S. Cl.
CPC ....... *A61F 13/15747* (2013.01); *B65H 37/04* (2013.01); *B65H 45/16* (2013.01);
(Continued)

(58) Field of Classification Search
CPC ... A61F 13/15747; B65H 37/04; B65H 45/16; B65H 45/165; B65H 45/28; B65H 2801/57
(Continued)

(56) References Cited

U.S. PATENT DOCUMENTS 3,848,594 A 11/1974 Buell
3,860,003 A 1/1975 Buell
(Continued)

FOREIGN PATENT DOCUMENTS

EP 0 812 789 A2 12/1997
WO WO 98/53779 A1 12/1998
(Continued)

OTHER PUBLICATIONS

13373 PCT International Search Report, dated Sep. 9, 2015, 10 pages.
(Continued)

*Primary Examiner* — Sameh Tawfik
(74) *Attorney, Agent, or Firm* — Andrew J. Hagerty; Sarah M. DeCristofaro

(57) ABSTRACT

A folding apparatus and method for forming a substrate including a discrete substrate including a rugosity. The folding apparatus may include a folding roll and a folding member. The folding roll includes an outer circumferential surface extending between the first roll surface and the second roll surface, and a receiving portion defined by the outer circumferential surface. The receiving portion may include an internal vacuum portion that may be operatively connected to an external vacuum portion. The folding member may be configured to associate with the receiving portion of the folding roll. The folding member may include a groove portion, a bonding portion, and a plurality of apertures. The folding apparatus may be used to bond a discrete substrate on a second substrate. The discrete substrate may include one or more rugosities.

4 Claims, 13 Drawing Sheets

(51) Int. Cl.
  *B65H 37/04* (2006.01)
  *B65H 45/28* (2006.01)
(52) U.S. Cl.
  CPC .......... *B65H 45/165* (2013.01); *B65H 45/28* (2013.01); *B65H 2801/57* (2013.01)
(58) Field of Classification Search
  USPC ....................................................... 493/442
  See application file for complete search history.

(56) References Cited

U.S. PATENT DOCUMENTS

| | | | |
|---|---|---|---|
| 3,905,592 A | 9/1975 | Spencer et al. | |
| 4,521,209 A * | 6/1985 | DuFresne | B65H 45/165 |
| | | | 493/418 |
| 4,610,678 A | 9/1986 | Weisman et al. | |
| 4,662,875 A | 5/1987 | Hirotsu et al. | |
| 4,673,402 A | 6/1987 | Weisman et al. | |
| 4,695,278 A | 9/1987 | Lawson | |
| 4,704,115 A | 11/1987 | Buell | |
| 4,739,910 A * | 4/1988 | Westphal | A61F 13/15585 |
| | | | 223/37 |
| 4,781,667 A * | 11/1988 | Kitai | B41F 13/56 |
| | | | 493/359 |
| 4,795,454 A | 1/1989 | Dragoo | |
| 4,834,735 A | 5/1989 | Alemany et al. | |
| 4,846,815 A | 7/1989 | Scripps | |
| 4,854,984 A | 8/1989 | Ball et al. | |
| 4,888,231 A | 12/1989 | Angstadt | |
| 4,894,060 A | 1/1990 | Nestegard | |
| 4,909,803 A | 3/1990 | Aziz et al. | |
| 4,919,738 A | 4/1990 | Ball et al. | |
| 4,946,527 A | 8/1990 | Battrell | |
| 5,004,451 A * | 4/1991 | Prum | B65H 45/167 |
| | | | 493/359 |
| 5,151,092 A | 9/1992 | Buell et al. | |
| 5,167,897 A * | 12/1992 | Weber | A61F 13/15593 |
| | | | 264/101 |
| 5,221,274 A | 6/1993 | Buell et al. | |
| 5,562,646 A | 10/1996 | Goldman et al. | |
| 5,599,335 A | 2/1997 | Goldman et al. | |
| 5,628,097 A | 5/1997 | Benson et al. | |
| 5,669,894 A | 9/1997 | Goldman et al. | |
| 5,693,165 A | 12/1997 | Schmitz | |
| 5,702,551 A | 12/1997 | Huber et al. | |
| 5,711,847 A | 1/1998 | Rajala et al. | |
| 5,817,199 A | 10/1998 | Brennecke et al. | |
| 5,916,661 A | 6/1999 | Benson et al. | |
| 6,107,539 A | 8/2000 | Palumbo et al. | |
| 6,123,792 A | 9/2000 | Samida et al. | |
| 6,248,195 B1 | 6/2001 | Schmitz | |
| 6,349,867 B1 | 2/2002 | Fernfors | |
| 6,450,321 B1 | 9/2002 | Blumenthal et al. | |
| 6,545,197 B1 * | 4/2003 | Muller | A61F 13/15203 |
| | | | 604/384 |
| 6,546,987 B1 | 4/2003 | Tachibana et al. | |
| 6,596,108 B2 | 7/2003 | McCabe | |
| 6,632,504 B1 | 10/2003 | Gillespie et al. | |
| 6,705,453 B2 | 3/2004 | Blumenthal et al. | |
| 6,790,798 B1 | 9/2004 | Suzuki et al. | |
| 6,811,019 B2 | 11/2004 | Christian et al. | |
| 6,814,217 B2 | 11/2004 | Blumenthal et al. | |
| 7,449,084 B2 | 11/2008 | Nakakado | |
| 7,452,321 B2 * | 11/2008 | Kauppila | B65H 45/24 |
| | | | 270/39.01 |
| 7,569,039 B2 | 8/2009 | Matsuda et al. | |
| 8,377,249 B2 | 2/2013 | Gill | |
| 8,617,341 B2 * | 12/2013 | Schneider | A61F 13/15747 |
| | | | 156/196 |
| 8,752,300 B2 | 6/2014 | Masek et al. | |
| 8,939,445 B2 * | 1/2015 | Schoultz | B65G 39/02 |
| | | | 162/367 |
| 9,655,790 B2 * | 5/2017 | Kurihara | A61F 13/51104 |
| 2002/0140151 A1 * | 10/2002 | Couturier | B65H 23/245 |
| | | | 270/58.07 |
| 2003/0021651 A1 | 1/2003 | Suzuki et al. | |
| 2004/0097895 A1 | 5/2004 | Busam et al. | |
| 2004/0158212 A1 | 8/2004 | Ponomarenko et al. | |
| 2005/0038401 A1 | 2/2005 | Suzuki et al. | |
| 2005/0107764 A1 | 5/2005 | Matsuda et al. | |
| 2007/0156110 A1 | 7/2007 | Thyfault | |
| 2009/0157035 A1 * | 6/2009 | Ponomarenko | A61F 13/15593 |
| | | | 604/385.24 |
| 2009/0312730 A1 | 12/2009 | LaVon et al. | |
| 2010/0069867 A1 * | 3/2010 | Noda | A61F 13/4756 |
| | | | 604/378 |
| 2012/0015791 A1 | 1/2012 | Yamamoto | |
| 2012/0061015 A1 | 3/2012 | LaVon et al. | |
| 2012/0061016 A1 | 3/2012 | LaVon et al. | |
| 2012/0152695 A1 | 6/2012 | Coenen et al. | |
| 2012/0226250 A1 * | 9/2012 | Sato | A61F 13/51104 |
| | | | 604/367 |
| 2013/0255861 A1 | 10/2013 | Schneider | |
| 2013/0255862 A1 | 10/2013 | Schneider et al. | |
| 2013/0255863 A1 | 10/2013 | LaVon et al. | |
| 2013/0255864 A1 | 10/2013 | Schneider et al. | |
| 2013/0255865 A1 | 10/2013 | Brown et al. | |
| 2014/0000794 A1 | 1/2014 | Hamilton et al. | |
| 2014/0000795 A1 | 1/2014 | Hamilton et al. | |
| 2014/0000798 A1 | 1/2014 | Hargett et al. | |
| 2014/0005021 A1 | 1/2014 | Walsh et al. | |
| 2014/0110053 A1 | 4/2014 | Ordway et al. | |
| 2014/0245865 A1 | 9/2014 | Masek et al. | |
| 2014/0336605 A1 | 11/2014 | Hardie et al. | |
| 2014/0377506 A1 | 12/2014 | Bao et al. | |
| 2014/0377513 A1 | 12/2014 | Galie et al. | |
| 2015/0088088 A1 * | 3/2015 | Wade | A61F 13/49012 |
| | | | 604/396 |
| 2015/0209195 A1 | 7/2015 | Martnus et al. | |
| 2015/0223995 A1 | 8/2015 | Martnus et al. | |
| 2015/0223996 A1 | 8/2015 | Martnus et al. | |
| 2015/0257946 A1 | 9/2015 | Martnus et al. | |
| 2015/0284892 A1 | 10/2015 | Galie et al. | |
| 2015/0342790 A1 | 12/2015 | Helton et al. | |

FOREIGN PATENT DOCUMENTS

| | | |
|---|---|---|
| WO | WO 2009/032995 A1 | 3/2009 |
| WO | WO 2014/120872 A1 | 8/2014 |

OTHER PUBLICATIONS

13372 PCT International Search Report, dated Sep. 9, 2015, 10 pages.
U.S. Appl. No. 14/572,861, filed Dec. 14, 2014, Martynus.
U.S. Appl. No. 14/572,871, filed Dec. 17, 2014, Martynus.
U.S. Appl. No. 14/572,886, filed Dec. 17, 2014, Martynus.
U.S. Appl. No. 14/572,894, filed Dec. 17, 2014, Martynus.
U.S. Appl. No. 14/247,276, filed Apr. 8, 2014, Galie.
U.S. Appl. No. 14/723,978, filed May 28, 2015, Helton.
U.S. Appl. No. 62/129,049, filed Mar. 6, 2015, Brown.
U.S. Appl. No. 62/129,050, filed Mar. 6, 2015, Brown.

* cited by examiner

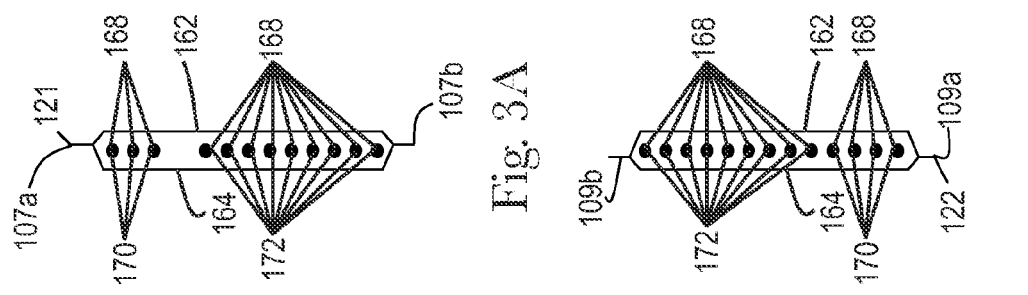
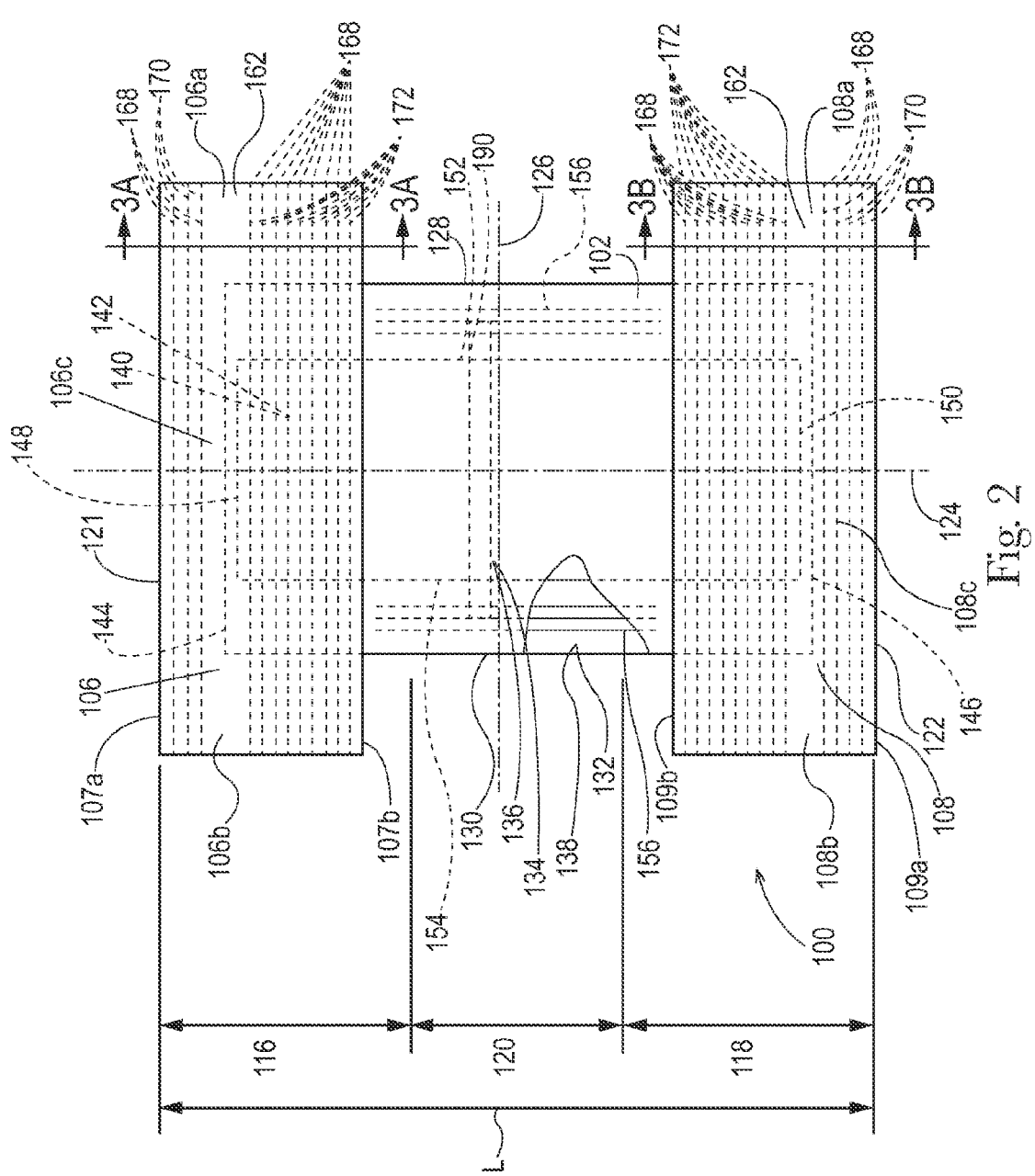

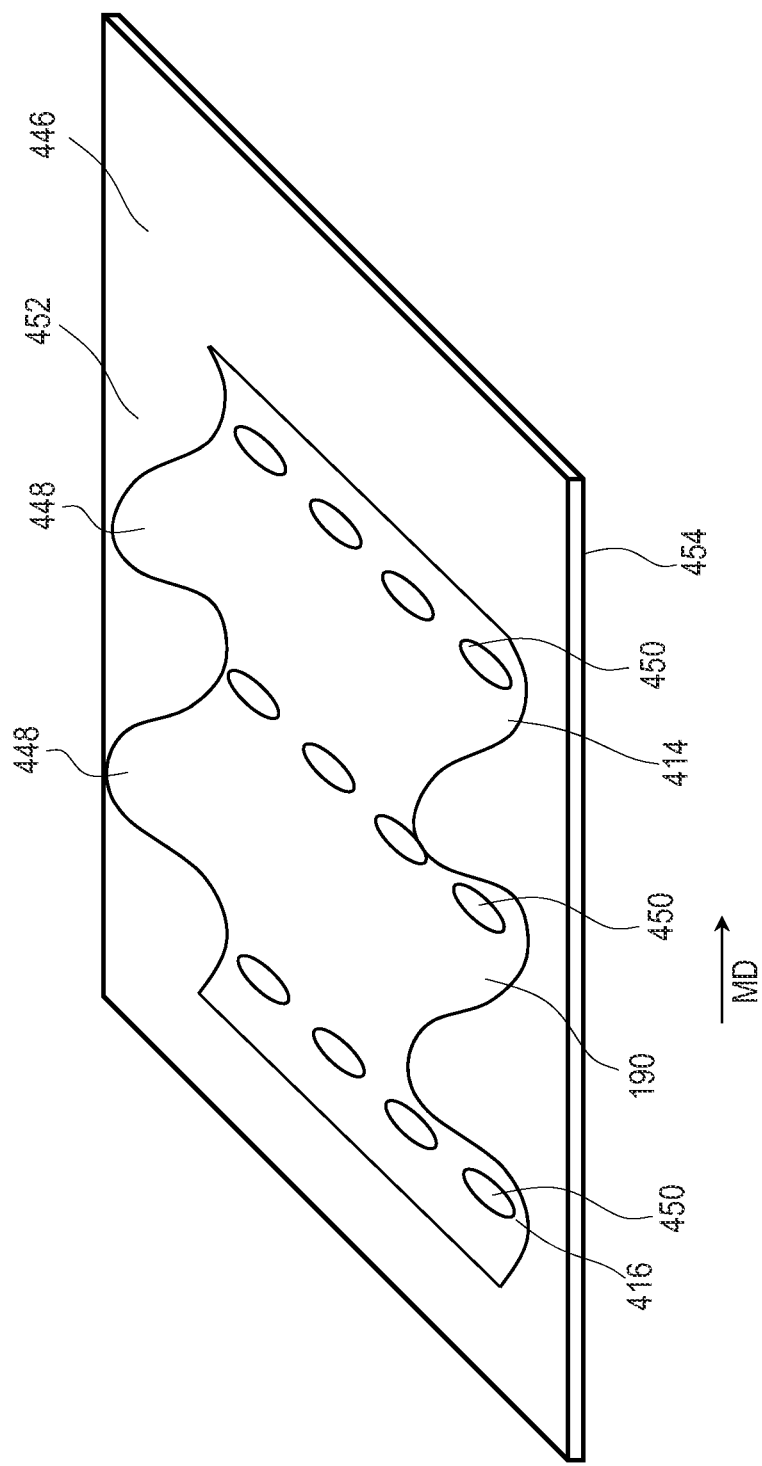

METHOD AND APPARATUS FOR MANUFACTURING AN ABSORBENT ARTICLE INCLUDING A DISCRETE SUBSTRATE HAVING A RUGOSITY

CROSS REFERENCE TO RELATED APPLICATION

This application claims the benefit of U.S. Provisional Application No. 62/004,240 filed on May 29, 2014, the substance of which is incorporated herein by reference.

FIELD OF THE INVENTION

The present disclosure relates to apparatuses and methods for manufacturing absorbent articles, and more particularly, apparatuses and methods for manufacturing absorbent articles including a discrete substrate having a rugosity.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of webs and components such as leg elastics, barrier leg cuff elastics, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

As mentioned above, during the assembly process, advancing webs of material may be combined with other advancing webs of material. Generally, these webs of material are combined to form absorbent articles that provide qualities such as desired fit, leakage protection, and relatively limited irritation to the skin of the wearer of the absorbent article. To accomplish these objectives, absorbent articles having an opening that provides a passageway to void space for collected feces and urine have been proposed. Similarly, absorbent articles having a barrier member to create separate areas for urine and feces have also been proposed. However, manufacturers are still looking for ways to improve these qualities of absorbent articles.

It has been found that manufacturing absorbent articles having additional component parts is expensive. For example, adding component parts may require additional material cost and equipment costs. Further, these absorbent articles are difficult to manufacture due to the complexity of adding additional component parts to the absorbent article while maintaining relatively high manufacturing speeds.

Further still, it has been found that using adhesives, such as glue, in absorbent articles has become increasingly undesirable. For example, adhesives have been known to cause skin irritation to the wearer of the absorbent articles.

Thus, a need exists for improved apparatuses and methods of manufacturing absorbent articles that include discrete substrates having a rugosity.

SUMMARY OF THE INVENTION

Aspects of the present disclosure relate to an apparatus and method for assembling absorbent articles. The apparatus may include a folding roll and a folding member. The folding roll may include a first roll surface, and a second roll surface opposite the first roll surface. At least one of the first roll surface and the second roll surface may define an external vacuum portion. An outer circumferential surface may extend between the first roll surface and the second roll surface. The outer circumferential surface may define a receiving portion. The receiving portion may include a side wall, a base surface, and an internal vacuum portion disposed on at least one of the side wall and the base surface. The external vacuum portion may be operatively connected to the internal vacuum portion. Further, the folding roll may be configured to rotate about a central longitudinal roll axis. The apparatus may also include a folding member configured to associate with the receiving portion of the folding roll. The folding member may include a first surface, a second surface opposite the first surface configured to associate with the base surface of the receiving portion, a first side surface, and a second side surface opposite the first side surface. The folding member may also include a groove portion, a plurality of apertures, and a bonding portion. The groove portion may be disposed in a portion of the first surface. The plurality of apertures may also be disposed on the first surface. The plurality of apertures may include a first portion of apertures adjacent to the first groove edge portion and a second portion of apertures disposed within the groove portion. At least one of the first side surface and the second side surface may include a vacuum portion operatively connected to a plurality of apertures. The bonding portion disposed on the first surface of the folding member.

In another embodiment, a method for forming a substrate including a discrete substrate having a rugosity may include the following steps: providing a folding roll including a folding member and an outer circumferential surface extending between a first roll surface and a second roll surface, wherein at least one of the first roll surface and the second roll surface comprise an external vacuum portion, and wherein the folding member comprises a leading edge portion, a trailing edge portion opposite the leading edge portion, a groove portion between the leading edge portion and the trailing edge portion and a plurality of apertures disposed on at least one of the leading edge portion, the trailing edge portion, and the groove portion, and wherein the plurality of apertures are fluidly connected to the external vacuum portion; advancing a discrete substrate comprising a leading edge portion, a trailing edge portion opposite the leading edge portion, and a central portion between the leading edge portion and the trailing edge portion; associating the leading edge portion of the discrete substrate with the leading portion of the folding member by activating a first vacuum port of the external vacuum portion; associating the central portion of the discrete substrate with the groove portion of the folding member by activating a second vacuum port of the external vacuum portion; associating the trailing portion of the discrete substrate with the trailing portion of the folding member by activating a third vacuum port of the external vacuum portion; advancing a substrate comprising a first substrate surface and a second substrate surface opposite the first substrate surface; and bonding the discrete substrate to at least one of the first substrate surface and the second substrate surface, wherein the discrete substrate bonded to the substrate forms a rugosity. The first, second, and third vacuum port may be activated sequentially.

BRIEF DESCRIPTION OF THE DRAWINGS

FIG. 2 is a partially cut away plan view of the diaper pant shown in FIG. 1;

FIG. 3A is a cross-sectional view of the diaper pant of FIG. 2 taken along line 3A-3A in accordance with one non-limiting embodiment of the present disclosure;

FIG. 3B is a cross-sectional view of the diaper pant of FIG. 2 taken along line 3B-3B in accordance with one non-limiting embodiment of the present disclosure;

FIG. 13 is a perspective view of a substrate including a discrete substrate having a rugosity in accordance with one non-limiting embodiment of the present disclosure.

DETAILED DESCRIPTION OF THE INVENTION

Figure 1:
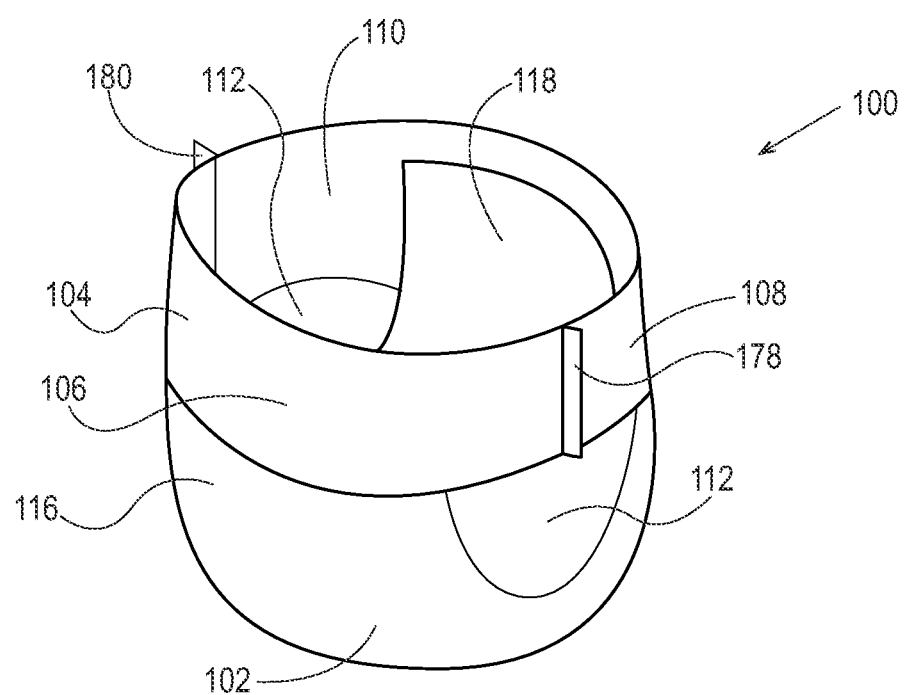
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant may be configured with a continuous or closed waist opening and at least one continuous, closed, leg opening prior to the article being applied to the wearer.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" is used herein to describe a material which is primarily two-dimensional (i.e., in an XY plane) and whose thickness (in a Z direction) is relatively small (i.e., 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material may be described as flowing in the machine direction through a process from upstream in the process to downstream in the process.

The term "cross direction" (CD) is used to herein refer to the direction perpendicular to the direction of material flow through a process. The cross direction may be substantially perpendicular to the machine direction.

The present disclosure relates to apparatuses and methods for manufacturing absorbent articles including a discrete substrate having a rugosity. More particularly, the apparatuses and methods are directed to manufacturing an absorbent article including a topsheet, a backsheet, a core, a first cuff, and a second cuff. As discussed in more detail below, the apparatuses and methods may include attaching a discrete substrate to a continuous substrate. More specifically, in some embodiments, the discrete substrate may be attached to the topsheet of an absorbent article. The discrete substrate may include one or more rugosities that may be used to aid in the separation of bodily exudates and/or the detainment of bodily exudates in certain portions of the absorbent article.

As discussed in more detail below, the apparatuses and methods according to the present disclosure may be utilized in the production of various components of absorbent articles, such as diapers. To help provide additional context to the subsequent discussion of the process embodiments, the following provides a general description of absorbent articles in the form of diapers that include components including the materials that may be used by the methods and apparatuses discussed herein.

Figure 4:
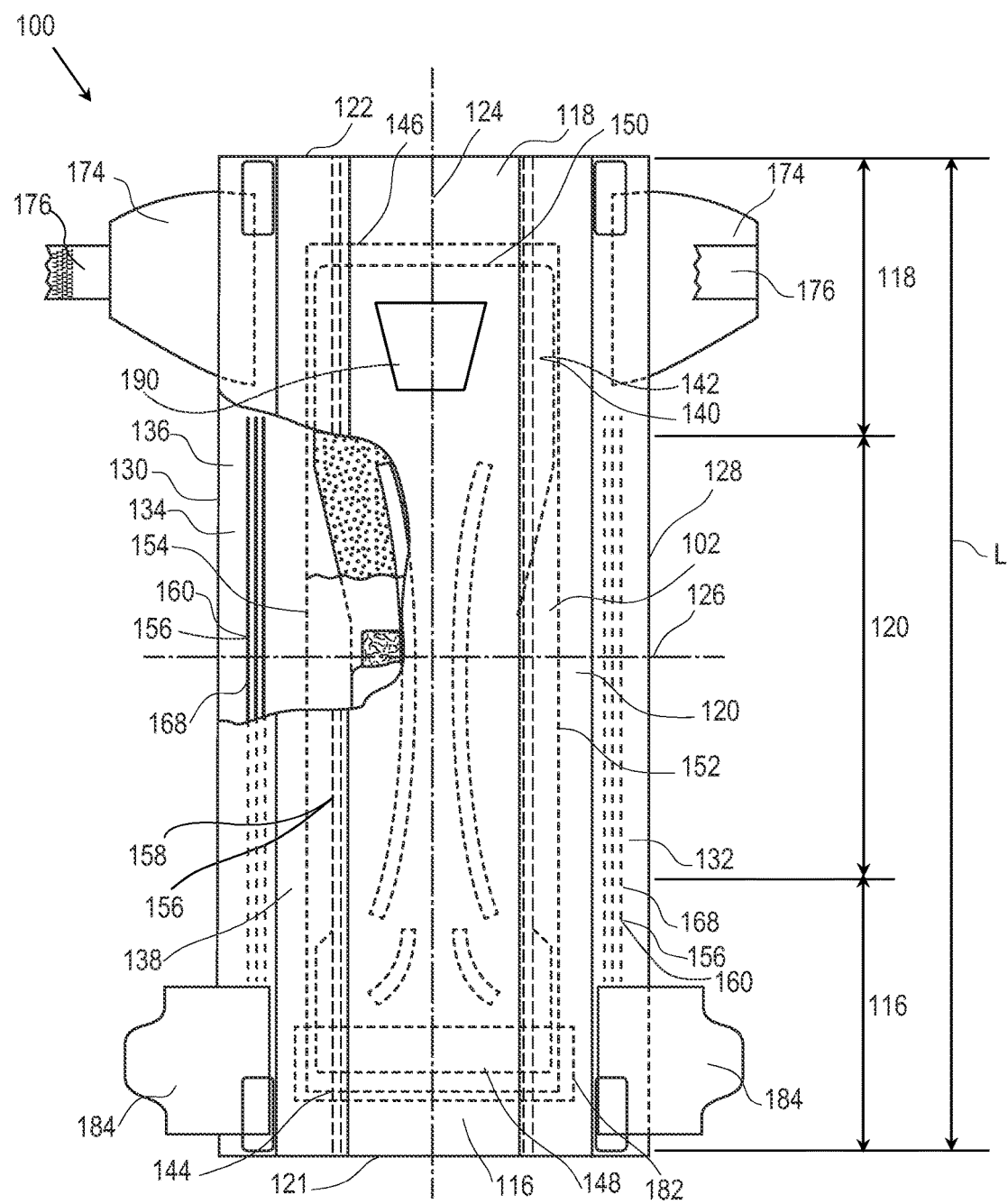
FIG. 4 is a partially cut away plan view of a diaper in accordance with one non-limiting embodiment of the present disclosure.

FIGS. 1, 2, and 4 illustrate an example of an absorbent article 100, such as a diaper, that may be assembled with the apparatuses and methods discussed herein. In particular, FIG. 1 shows a perspective view of an absorbent article 100 in a pre-fastened configuration, and FIG. 2 shows a plan view of the absorbent article 100 with the portion of the diaper that faces away from a wearer oriented towards the viewer. The absorbent article 100 shown in FIGS. 1 and 2 includes a chassis 102 and a ring-like elastic belt 104. As discussed below in more detail, a first elastic belt 106 and a second elastic belt 108 are connected together to form the ring-like elastic belt 104.

With continued reference to FIG. 2, the chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region 120 may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the absorbent article 100 and chassis 102 of FIG. 2 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1, 2 and 4, the absorbent article 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the absorbent article 100 may also include other features, such as leg elastics and/or leg cuffs to enhance the fit around the legs of the wearer.

The periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. When the absorbent article 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. Moreover, the crotch region 120 may be generally positioned between the legs of the wearer with the absorbent core 142 extending from the front waist region 116 through the crotch region 120 to the back waist region 118.

It is also to be appreciated that a portion or the whole of the absorbent article 100 may also be made laterally extensible. The additional extensibility may help allow the absorbent article 100 to conform to the body of a wearer during movement by the wearer. The additional extensibility may also help, for example, allow the diaper 100, including a chassis 102 having a particular size before extension, to extend in the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas, and undergarments. The backsheet 136 may also include a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also include an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the absorbent article 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets, and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

The absorbent article 100 may also include an absorbent assembly 140 that is joined to the chassis 102. As shown in FIGS. 2 and 4, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core may comprise a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

The absorbent article 100 may also include elasticized leg cuffs 156. It is to be appreciated that the leg cuffs 156 may be and are sometimes also referred to as leg bands, side flaps, barrier cuffs, elastic cuffs, or gasketing cuffs. The elasticized leg cuffs 156 may be configured in various ways to help reduce the leakage of body exudates in the leg regions. For example, in some embodiments, a gasketing leg cuff 160 may be positioned adjacent to the side edge 130, 128 of the chassis 102 and a barrier leg cuff 158 may be positioned between a gasketing leg cuff 160 and the longitudinal axis 124 of the absorbent article 100. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730A1; and U.S. Patent Publication No. 2013/0255865A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, the absorbent article may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2, 3A, and 3B, the belt elastic material may include a plurality of elastic strands 168 that may be referred to herein as outer, waist elastics 170 and inner, waist elastics 172.

As shown in FIG. 2, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

Referring to FIG. 4, in some embodiments, the absorbent article 100 may include a fastening system. The fastening system can be used to provide lateral tensions about the circumference of the absorbent article to hold the absorbent article on the wearer. The fastening system may comprise a fastener such as tape tabs, hook and loop fastening components, interlocking fasteners such as tabs and slots, buckles, buttons, snaps, and/or hermaphroditic fastening components. A landing zone 182 may be provided on the front waist region 116 for at least a portion of the fastener to be releasably attached to. Exemplary fastening systems may include those described in U.S. Pat. Nos. 3,848,594; 4,662, 875; 4,846,815; 4,894,060; 4,946,527; 5,151,092; and 5,221,274.

As illustrated in FIG. 4, the absorbent article 100 may comprise front ears 184 and back ears 174. The front ears 184 and the back ears 174 may be an integral part of the chassis 102. For example, the front ears 184 and the back ears 174 may be formed from the topsheet 138 and/or the backsheet 136. Alternatively, the front ears 184 and the back ears 174 may be attached to the backsheet 136 and/or the topsheet 138. The front ears 184 and the back ears 174 may be extensible to facilitate attachment on the landing zone 182 and to maintain placement around the waist of the wearer. The back ears 174 may comprise a tab member 176. The tab member 176 may be attached to a portion of the back ears 174 to facilitate attachment to the landing zone 182.

The absorbent article 100 may also comprise a discrete substrate 190, as illustrated in FIGS. 2 and 4. An exemplary discrete substrate may include that described in U.S. Patent Application Nos. 61/918,954; 61/919,067; 61/918,966; and 61/918,978. In some exemplary embodiments, the discrete substrate 190 may be positioned in the crotch region 120 of the absorbent article 100, as illustrated in FIG. 2. More specifically, the discrete substrate 190 may be positioned a distance from the front edge 121 of the absorbent article 100. The distance may be 25% to 50% and/or 30% to 45% of the total length L of the absorbent article 100 taken from the front edge 121 to the rear edge 122 of the absorbent article 100. The discrete substrate 190 may be positioned such that it extends substantially perpendicular to the longitudinal axis 124 of the absorbent article 100. Similarly, the discrete substrate 190 may be positioned such that it extends substantially parallel to the lateral axis 126 of the absorbent article 100. The discrete substrate 190 may be extensible in at least one of the longitudinal direction and the lateral direction. In some exemplary embodiments, the discrete substrate 190 may be disposed on at least one of the front waist region 116, the back waist region 118, and the crotch region 120. As illustrated in FIG. 4, the discrete substrate 190 may be disposed on a portion of the back waist region 118. The discrete substrate 190 may be placed in any position on the absorbent article 100 that aids in the functionality of the absorbent article, such as by providing increased absorbency and increased containment of bodily exudates. Further, the discrete substrate 190 may be any shape and contain any number of rugosities that aid in the functionality of the absorbent article. The discrete substrate 190 will be discussed in more detail herein.

As previously mentioned, the apparatuses and methods according to the present disclosure may be utilized to assemble discrete absorbent articles 100 and/or various components of absorbent articles 100, such as for example, chassis 102, elastic belts 106, 108, leg cuffs 156, and/or discrete barrier members 190. Although the following methods may be provided in the context of absorbent articles 100, as shown in FIGS. 1, 2, and 4, it is to be appreciated that the methods and apparatuses herein may be used with various process configurations and/or absorbent articles, such as for example, disclosed in U.S. Pat. No. 7,569,039; U.S. Patent Publication Nos. 2005/0107764A1, 2012/0061016A1, and 2012/0061015A1; 2013/0255861A1; 2013/0255862A1; 2013/0255863A1; 2013/0255864A1; and 2013/0255865A1.

Figure 5:
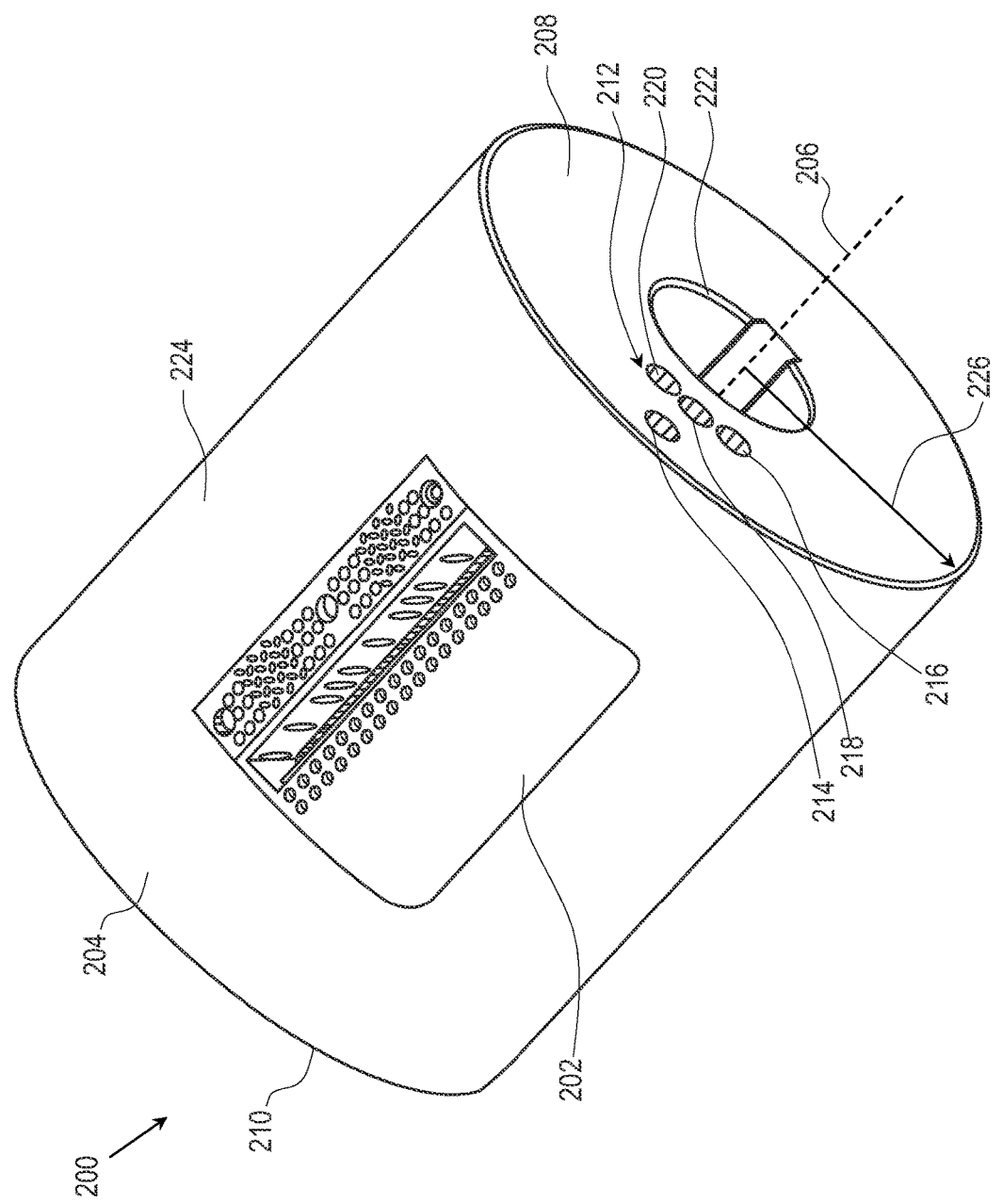
FIG. 5 is a perspective view of the folding roll including a folding member in accordance with one non-limiting embodiment of the present disclosure.

FIG. 5 shows an exemplary schematic representation of an apparatus that may be used to manufacture an absorbent article 100, as previously described, including a discrete substrate 190. More specifically, the folding apparatus 200 may be used to form a substrate comprising a discrete substrate 190. The discrete substrate 190 may include a rugosity. The folding apparatus 200 may include a folding member 202. The folding roll 204 may be configured to associate with a discrete substrate, fold the discrete substrate, and deposit the discrete substrate onto an advancing substrate. In some exemplary embodiments, the folding member 202 may be disposed on a portion of a folding roll 204. The folding roll 204 may be configured to rotate about a central longitudinal roll axis 206, which may cause the folding member 202 to rotate.

Still referring to FIG. 5, the folding roll 204 may include a first roll surface 208 and a second roll surface 210, opposite the first roll surface 208. At least one of the first roll surface 208 and the second roll surface 210 may include an external vacuum portion 212. The external vacuum portion 212 may include one or more external vacuum ports that are configured to operatively engage a vacuum device, which may pull fluid through the external vacuum port toward the vacuum device. In some embodiments, as shown in FIG. 5, the external vacuum portion 212 may include a first external vacuum port 214, a second external vacuum port 216, a third external vacuum port 218, and a forth external vacuum port 220. It is to be appreciated that there may be any number of external vacuum ports that make up the external vacuum portion 212. The number of external vacuum ports may depend on, for example, the amount of vacuum needed and the size of each of the vacuum ports.

The first roll surface 208 and the second roll surface 210 may each define a shaft opening 222. The shaft opening 222 may extend through the folding roll 204. The shaft opening 222 be configured to receive a shaft, not shown, which may be used to rotate the folding roll 204.

The folding roll 204 may also include an outer circumferential surface 224 that extends between the first roll surface 208 and the second roll surface 210. The outer circumferential surface 224 may extend radially outward from the central longitudinal roll axis 206. More specifically, the outer circumferential surface 224 may be positioned at an outer radius 226 from the central longitudinal roll axis 206. In some example embodiments, the outer radius 226 may be from about 75 mm to about 225 mm and/or from about 90 mm to about 200 mm and/or from about 100 mm to about 190 mm.

The folding roll 204 may be made from a number of materials including, but not limited to, metals and polymers. For example, 3D printing with polymers or powdered metals may be used to form a portion of the folding roll or the entire folding roll. In some example embodiments, at least a portion of the folding roll 204 may be manufactured with hardened steel.

Figure 6:
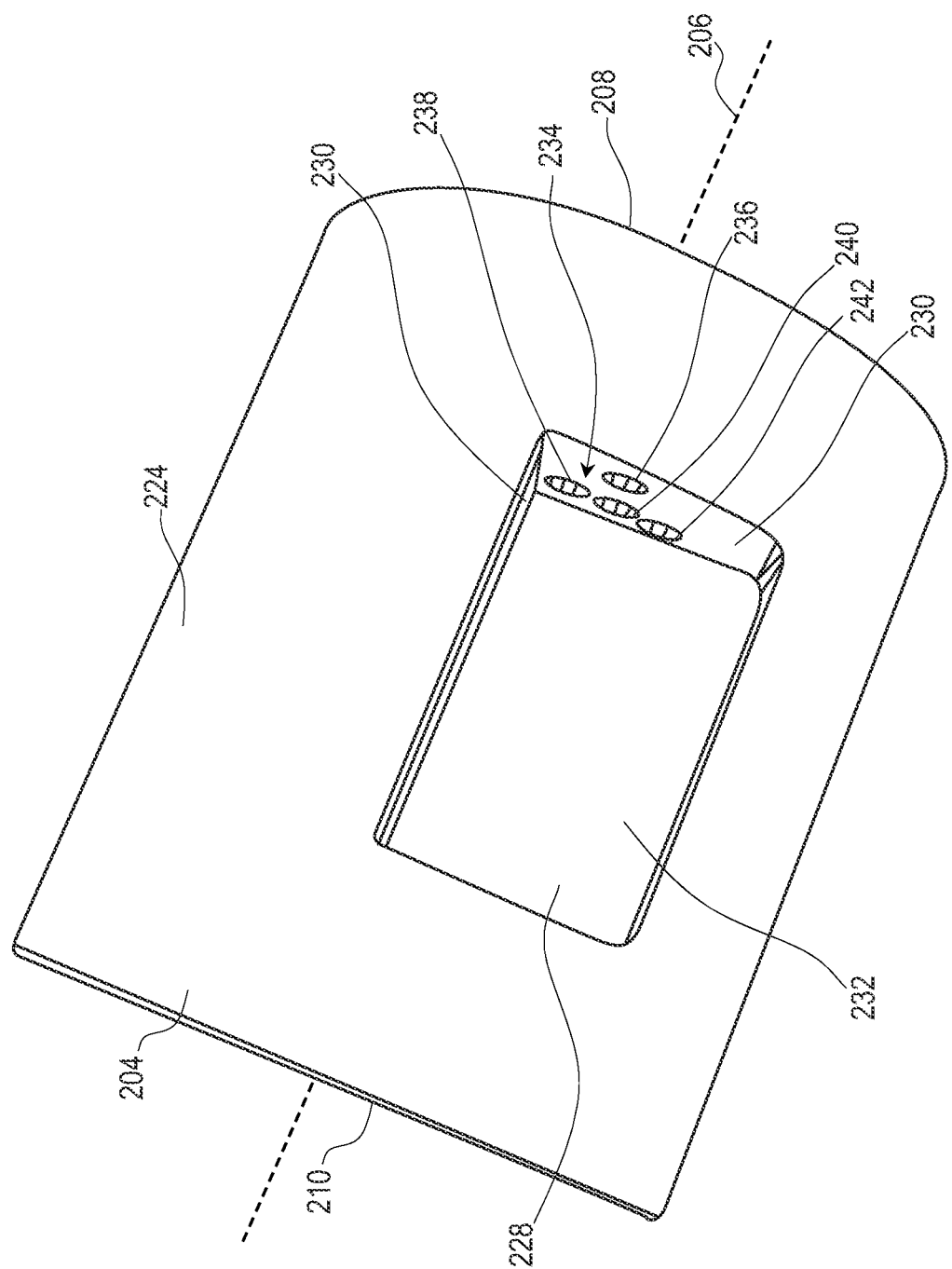
FIG. 6 is a perspective view of a folding roll in accordance with one non-limiting embodiment of the present disclosure.

As previously stated, the folding roll 204 may include a folding member 202, as shown in FIG. 5. The folding member 202 may be manufactured as part of the folding roll 204. Thus, the folding member 202 may not be removeable from the folding member 202. However, in some embodiments, the folding member 202 may be removably associated with the folding roll 204. Thus, the folding roll 204 may include a receiving portion 228 defined by the outer circumferential surface 224, as illustrated in FIG. 6. The receiving portion 228 may be sized to accept the folding member 202. The receiving portion 228 may include side walls 230 and a base surface 232. The side walls 230 and base surface 232 may be configured to surround the folding member 202 such that it is secure during operation. One or more of the side walls 230 may include an internal vacuum portion 234. The internal vacuum portion 234 may include an internal vacuum port. The internal vacuum portion 234 may include any number of internal vacuum ports. The number of internal vacuum ports may depend on, for example, the amount of vacuum needed, the size of each of the vacuum ports, and/or the number of external vacuum ports. For example, as shown in FIG. 6, the internal vacuum portion 234 may include a first internal vacuum port 236, a second internal vacuum port 238, a third internal vacuum port 240, and a fourth internal vacuum port 242.

The internal vacuum portion 234 may be operatively connected to the external vacuum portion 212, as shown in FIG. 5. More specifically, for example, the first external vacuum port 214 may be fluidly connected to the first internal vacuum port 234, the second external vacuum port 216 may be fluidly connected to the second internal vacuum port 238, the third external vacuum port 218 may be fluidly connected to the third internal vacuum port 240, and/or the fourth external vacuum port 220 may be fluidly connected to the fourth internal vacuum port 242. However, it is to be appreciated that the number of external vacuum ports may not match the number of internal vacuum ports. Thus, for example, more than one external vacuum port may be connected to a single internal vacuum port and vice versa. Similarly, not every external vacuum port needs to be fluidly connected to an internal vacuum port. The number and connection of internal and external vacuum ports will depend partly on the amount of vacuum that needs to be placed on the discrete substrate to achieve the desired deformation. Fluidly connected means that a fluid may move from one port to another port.

It is to be appreciated that the receiving portion 228 may be designed in view of the folding member 202. Thus, the receiving portion 228 may be sized to accept the folding member 202. For example, as shown in FIG. 7, the receiving portion 228 may be configured such that the folding member 202 may slidably engage the folding roll 204.

Figure 7:
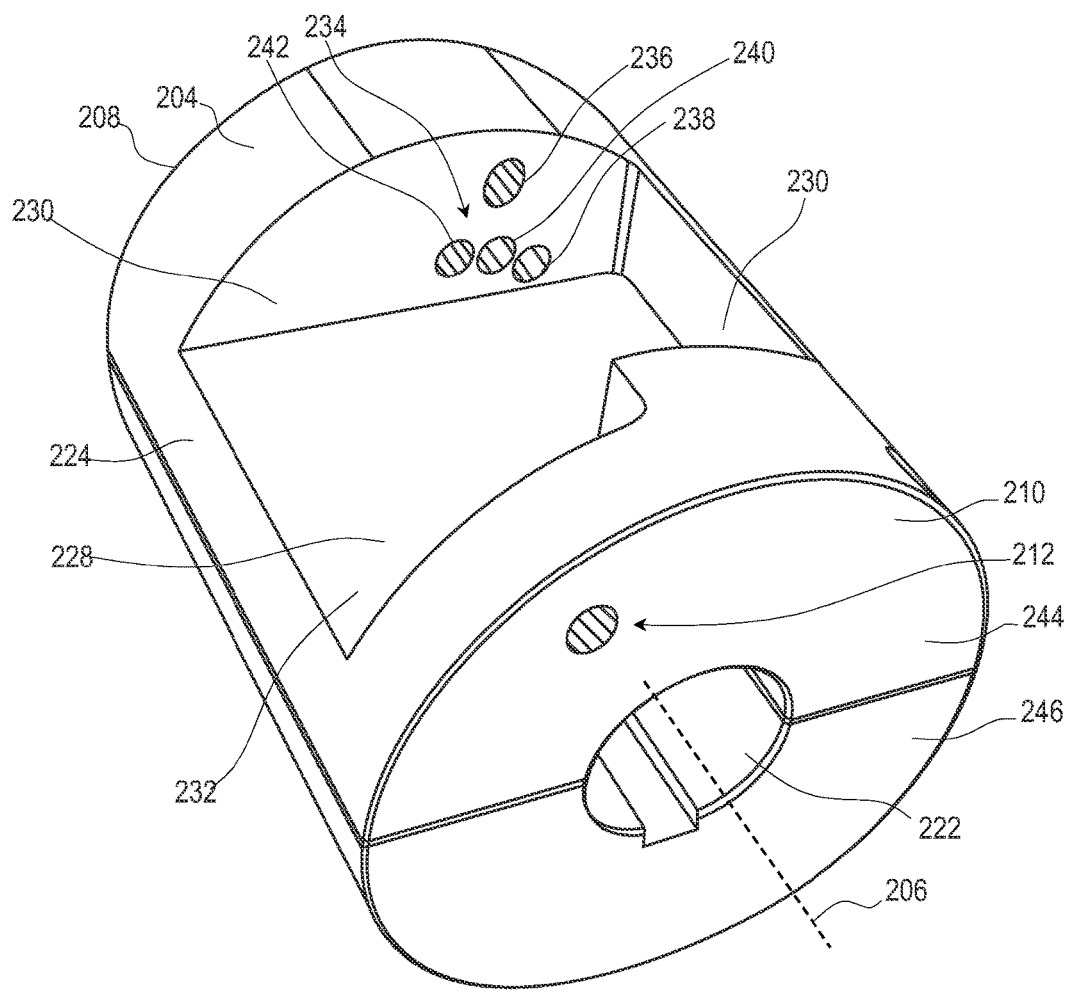
FIG. 7 is a perspective view of a folding roll in accordance with one non-limiting embodiment of the present disclosure.

Still referring to FIG. 7, as previously discussed, the folding roll 204 may be used for high speed manufacture of absorbent articles, such as diapers. Thus, the folding roll 204 and/or the folding member 202 may be designed such that each may be readily repaired and/or replaced. For example, the folding roll 204 may be assembled in any number of pieces such that each piece may be independently replaced. FIG. 7 illustrates a folding roll 204 comprising a first roll portion 244 and a second roll portion 246. The first roll portion 244 and the second roll portion 246 may be associated with one another mechanically and/or chemically. For example, the first roll portion 244 and the second roll portion 246 may be mechanically associated with screws or clamps. Similarly, the first roll portion 244 and the second roll portion 246 may be chemically associated with adhesives.

Figure 8:
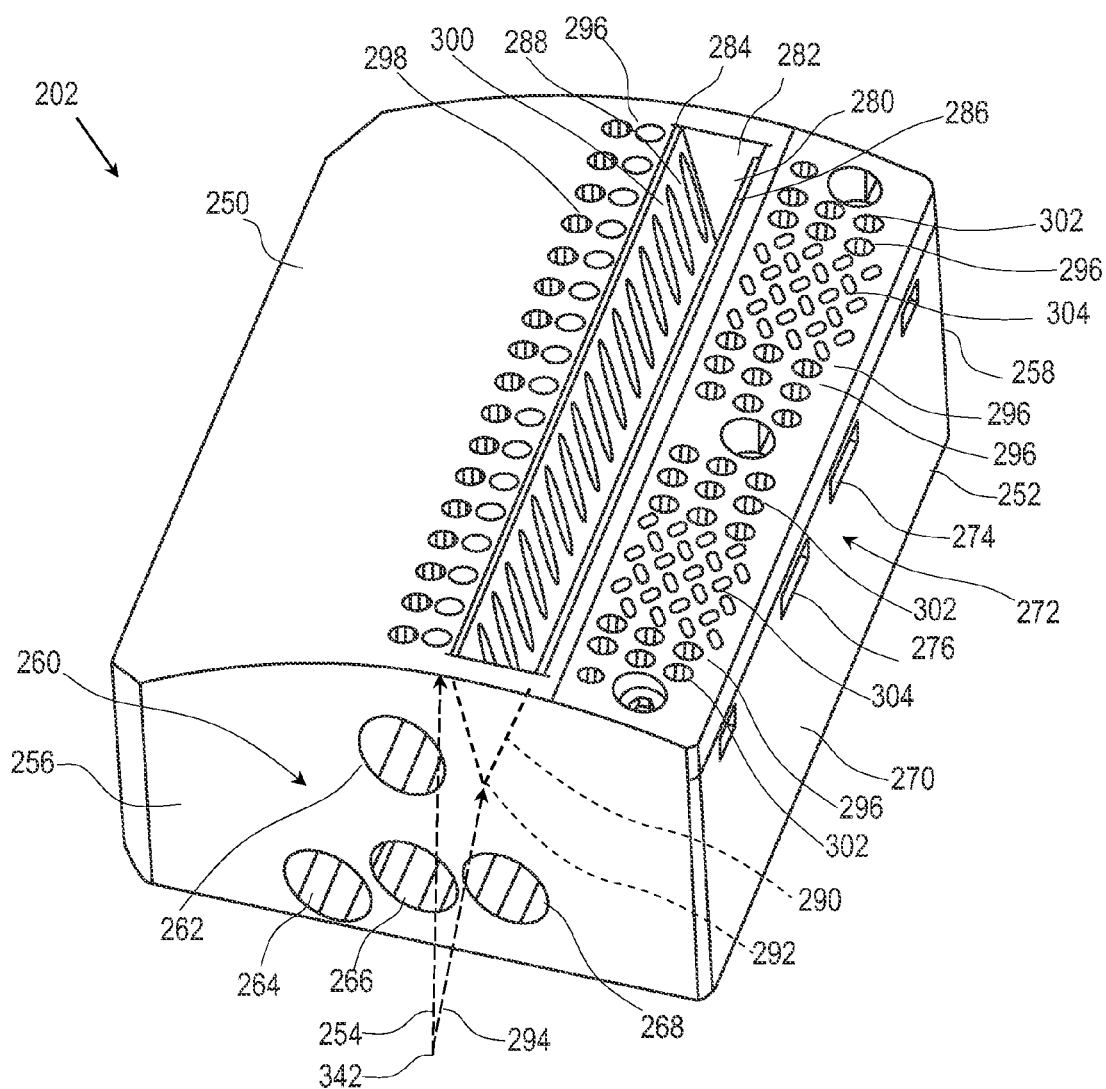
FIG. 8 is a perspective view of a folding member in accordance with one non-limiting embodiment of the present disclosure.

As illustrated in FIG. 8, the folding member 202 may include a first surface 250 and a second surface 252, opposite the first surface 250. The second surface 252 may be configured to associate with the base surface 232 of the receiving portion 228 of the folding roll 204, as shown in FIG. 5. The first surface 250 may include a first surface radius 254. The first surface radius 254 may be a predetermined value that is used in the design of the folding member 202. Thus, the first surface radius 254 defines a center 342 radius of curvature of the first surface 250. The first surface radius 254 may be the same as the outer radius 226 of the outer circumferential surface 224 of the folding roll 204. Thus, the first surface radius 254 may share the same center 342 as the outer radius 266 of the outer circumferential surface 224. In some embodiments, the first surface radius 254 may be less than or greater than the outer radius 226 of the outer circumferential surface 224 of the folding roll 204. The first surface 250 of the folding member 202 may be substantially planar with the outer circumferential surface 224 of the folding roll 204. In some embodiments, the first surface 250 or at least a portion of the first surface 250 may be substantially flat such that there is not a radius of curvature to the first surface.

The folding member 202 may also include a first side surface 256 and a second side surface 258, opposite the first side surface 256. At least one of the first side surface 256 and the second side surface 258 may include a vacuum portion 260. The vacuum portion 260 may include one or more vacuum ports. For example, as shown in FIG. 8, the folding member 202 may include at a first side surface 256 including a vacuum portion 260 comprising a first vacuum port 262, a second vacuum port 264, a third vacuum port 266, and a fourth vacuum port 268. The vacuum portion 260 of the folding member 202 may be fluidly connected with the internal vacuum portion 234 of the folding roll 204. In some embodiments, for example, the first vacuum port 262 may be fluidly connected to the first internal vacuum port 236, the second vacuum port 264 may be fluidly connected to the second internal vacuum port 238, the third vacuum port 266 may be fluidly connected to the third internal vacuum port 240, and/or the fourth vacuum port 268 may be fluidly connected to the fourth internal vacuum port 242.

The folding member 202 may also include a third side surface 270. The third side surface 270 may extend between the first side surface 256 and the second side surface 258. The third side surface 270 may also include a second vacuum portion 272. The second vacuum portion 272 may include one or more vacuum ports. For example, as shown in FIG. 8, the second vacuum portion 272 may include a fifth vacuum port 274 and/or a sixth vacuum port 276. The second vacuum portion 272 may be fluidly connected to another internal vacuum portion (not shown). It is to be appreciated that a vacuum portion including one or more vacuum ports may be placed at any position on the folding member 202 such that vacuum is applied at the appropriate portion of the folding member 202.

Still referring to FIG. 8, the folding member 202 may also include a groove portion 280. The groove portion 280 may be configured to form a rugosity in the discrete substrate. The groove portion 280 may be disposed in a portion of the first surface 250 of the folding member 202. The groove portion 280 may include a first groove 282. The first groove 282 may include a first groove edge portion 284 and a second groove edge portion 286. In some embodiments, the first groove edge portion 284 may be substantially parallel to the second groove edge portion 286. The first groove edge 284 and/or the second groove edge may be positioned a radius equal to the first surface radius 254. In some embodiments, the first groove edge portion 284 and/or the second groove edge portion 286 may be substantially planar with the outer circumferential surface of the folding roll 202.

The first groove 282 may extend from the first groove edge portion 284 to the second groove edge portion 286. More specifically, the first groove 282 may include a first face 288 extending from the first groove edge portion 284 and a second face 290 extending from the second groove edge portion 286. The first face 288 and the second face 290 may converge at a base portion 292. The base portion 292 may be the point at which the first face 288 and the second face 290 converge. Alternatively, the base portion 292 may be a substantially planar portion having a flat surface. Further, the base portion 292 may include a curved portion. It is to be appreciated that the profile of the base portion 292 may be designed to obtain a desired profile in the discrete substrate and/or to obtain the desired vacuum on the discrete substrate. The base portion 292 may be positioned at a first inner radius 294. The first inner radius 294 may be less than the first surface radius 254. The groove portion 280 provides an area in which the discrete substrate is deflected to form a rugosity.

The folding member 202 may also include a plurality of apertures 296. The plurality of apertures 296 may include one or more portions of apertures. For example, as shown in FIG. 8, a first portion of apertures 298 may be disposed adjacent to the first groove edge portion 284 and a second portion of apertures 300 may be disposed within the groove portion 300. Further, in some example embodiments, a third portion of apertures 302 may be disposed adjacent to the second groove edge portion 286. Each of the plurality of apertures 296 may be fluidly connected to at least one vacuum portion 260, 272. In some embodiments, the first vacuum port 262 may be fluidly connected with the first portion of apertures 298, the second vacuum port 264 and the third vacuum port 266 may be fluidly connected to the second portion of apertures 300, and the fourth vacuum port 268 may be fluidly connected to at least one of the second portion of apertures 300 and the third portion of apertures 302. Further, in some embodiments, the fifth vacuum port 274 and the sixth vacuum port 276 may be fluidly connected to the third portion of apertures 302. Each of the plurality of apertures 296 may have a cross sectional shape. The cross sectional shape may be any shape that allows a vacuum force to act on the discrete substrate. Similarly, each of the plurality of apertures may have a size. The size of each aperture may depend on the desired vacuum force to be applied to the discrete substrate, the spacing constraints on the first surface 250 of the folding member 202, and/or the ability to connect each aperture with a vacuum portion.

The folding member 202 may also include a bonding portion 304. The bonding portion 304 may be configured to attach the discrete substrate to another substrate, such as a continuous substrate. The bonding portion 304 may be designed such that various types of bonding methods may be used such as high pressure welding, hot air welding, heated crimping, and rotary ultrasonic welding. Exemplary bonding methods and apparatuses may include those described in U.S. Pat. Nos. 4,854,984; 4,919,738; 5,711,847; 5,817,199; 6,123,792; 7,449,084; 6,248,195; 6,546,987; and U.S. patent application Ser. Nos. 14/038,812; 61/836,690; and 61/836,745. The bonding portion 304 may be made from the same material as the folding member 202 and/or at least the first surface 250 of the folding member 202. In some embodiments, the bonding portion 304 may be made from a material other than the material used make the folding member 202. For example, the folding member 202 may be made from plastic and the bonding porting may be made from metal. The bonding portion 304 may be made from a different material than the other portions of the folding member 202 due to, for example, the heat and/or the pressure used to bond the discrete substrate to another substrate.

The bonding portion 304 may be disposed on the first surface 250 of the folding member 202. In some embodiments, as shown in FIG. 8, the bonding portion 304 may be interposed between the plurality of apertures 296. More specifically, the bonding portion 304 may be adjacent to the second groove edge portion 286 and adjacent to the third portion of apertures 302. It is to be appreciated that the bonding portion 304 may be placed is any position on the first surface 250 where the discrete substrate may be bonded to the continuous substrate. The position of the bonding portion 304 may depend on the final structure of the discrete substrate. For example, if the discrete substrate is to have two rugosities, the folding member 202 may be required to have more than two bonding portions 304 disposed on the first surface 250. Further, in some embodiments, the bonding portion 304 may be substantially planar with the first surface 250 and/or the boding portion 304 may protrude above the first surface 250. The distance the bonding portion 304 protrudes above the first surface 250 may depend on the material properties of the substrate and/or the thickness of the substrate. In some embodiments, the bonding portion may protrude about 0.5 mm above the first surface 250.

Figure 9A:
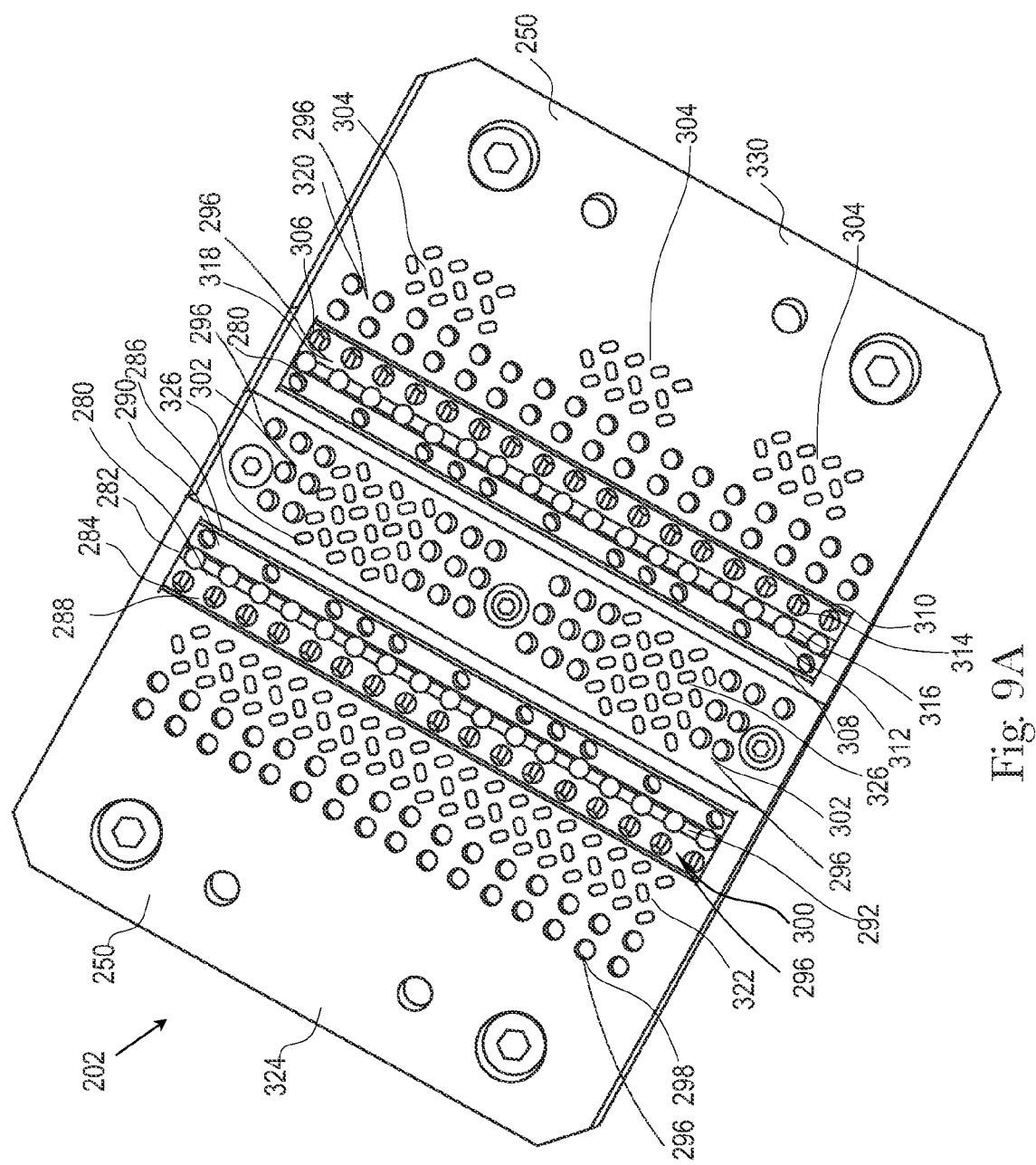
FIG. 9A is a perspective view of a folding member in accordance with one non-limiting embodiment of the present disclosure.

Referring to FIG. 9A, the folding member 202 may include a groove portion 280. The groove portion 280 may include a first groove 282 and a second groove 306. The second groove 306 may be positioned substantially parallel to the first groove 282. However, it is to be appreciated that the position of the first groove 282 and the second groove 306 may depend on the desired structure of the discrete substrate. Thus, the first groove 282 and the second groove 306 may be positioned at an angle to one another.

The second groove 306 may include a first groove edge portion 308 and a second groove edge portion 310. In some embodiments, the first groove edge portion 308 may be substantially parallel to the second groove edge portion 310. The second groove 306 may include a first face 312, a second face 314, and a base portion 316. The first face 312 may extend from the first groove edge portion 308 to the base portion 316. Similarly, the second face 314 may extend from the second groove edge portion 310 to the base portion 316.

The folding member 202 may also include a plurality of apertures 296. The plurality of apertures 296 may be disposed on the first surface 250 and be fluidly connected to at least one vacuum portion, which includes at least one vacuum port. The plurality of apertures 296 may be positioned on the first surface 250 of the folding member 202 such that the discrete substrate may be held on the first surface of the folding member 202 and at least a portion of the discrete substrate may deflect into the groove portion forming a rugosity. For example, as shown in FIG. 9A, a first portion of apertures 298 may be positioned on the leading edge portion 324 and/or adjacent to the first groove edge portion 284. A second portion of apertures 300 may be positioned in the first groove 282. More specifically, the second portion of apertures 300 may be present on at least one of the first face 288, the second face 290, and the base portion 292 of the first groove 282. The second portion of apertures 300 may be uniformly spaced across the width of the first groove 282 or, alternately, non-uniformly across the width of the first groove 282. A third portion of apertures 302 may be positioned between the first groove 282 and the second groove 306. Further, a fourth portion of apertures 318 may be positioned within the second groove 306. More specifically, the fourth portion of apertures 318 may be present on the first face 312, the second face 314, and the base portion 316 of the second groove 306. The fourth portion of apertures 318 may be uniformly spaced across the width of the second groove 306 or, alternately, non-uniformly across the width of the second groove 306. Further still, a fifth portion of apertures 320 may be positioned adjacent to the second groove edge portion 310 of the second groove 306.

The folding member 202 may also include a bonding portion 304. The bonding portion 304 may be positioned such that when the discrete substrate is bonded to another substrate, the discrete substrate maintains the rugosities created by the folding member 202. In some embodiments, a bonding portion 304 may be positioned around each groove. For example, as shown in FIG. 9A, a first bonding portion 322 may be positioned on the leading edge portion 324 of the folding member 202 and/or between the first portion of apertures 296 and the first grove portion 282. A second bonding portion 326 may be positioned between each of the first groove 282 and the second groove 306. Further, in some embodiments, the second bonding portion 326 may be interposed between a portion of apertures. It is to be appreciated that the second bonding portion 326 may be positioned along a side of the portion of apertures or in any other position that creates the desired bond pattern in the discrete substrate. A third boding portion 328 may be positioned on a trailing edge portion 330 and/or adjacent to the second groove 306 of the folding member 202.

It is to be appreciated that in some embodiments, the folding member 202 may be disposed on a folding roll 204 that rotates the folding member 202 about a central longitudinal roll axis 206, as previously discussed. The direction of rotation of the folding member 202 may be important when determining where to place the portion of apertures, which are configured to impart a vacuum force on the discrete substrate. For example, the leading edge portion 324 may be the portion of the folding member 202 that leads during rotation and is opposite to the trailing edge portion 330 which follows the leading edge portion during rotation. In some embodiments, a portion of apertures should be disposed closest to the leading edge portion 324 so that when the folding member 202 associates with the discrete substrate, the discrete substrate is drawn to the folding member 202 and the leading edge portion of the discrete substrate may be prevented from furrowing or wrinkling against the first surface 250 of the folding member 202.

Figure 9B:
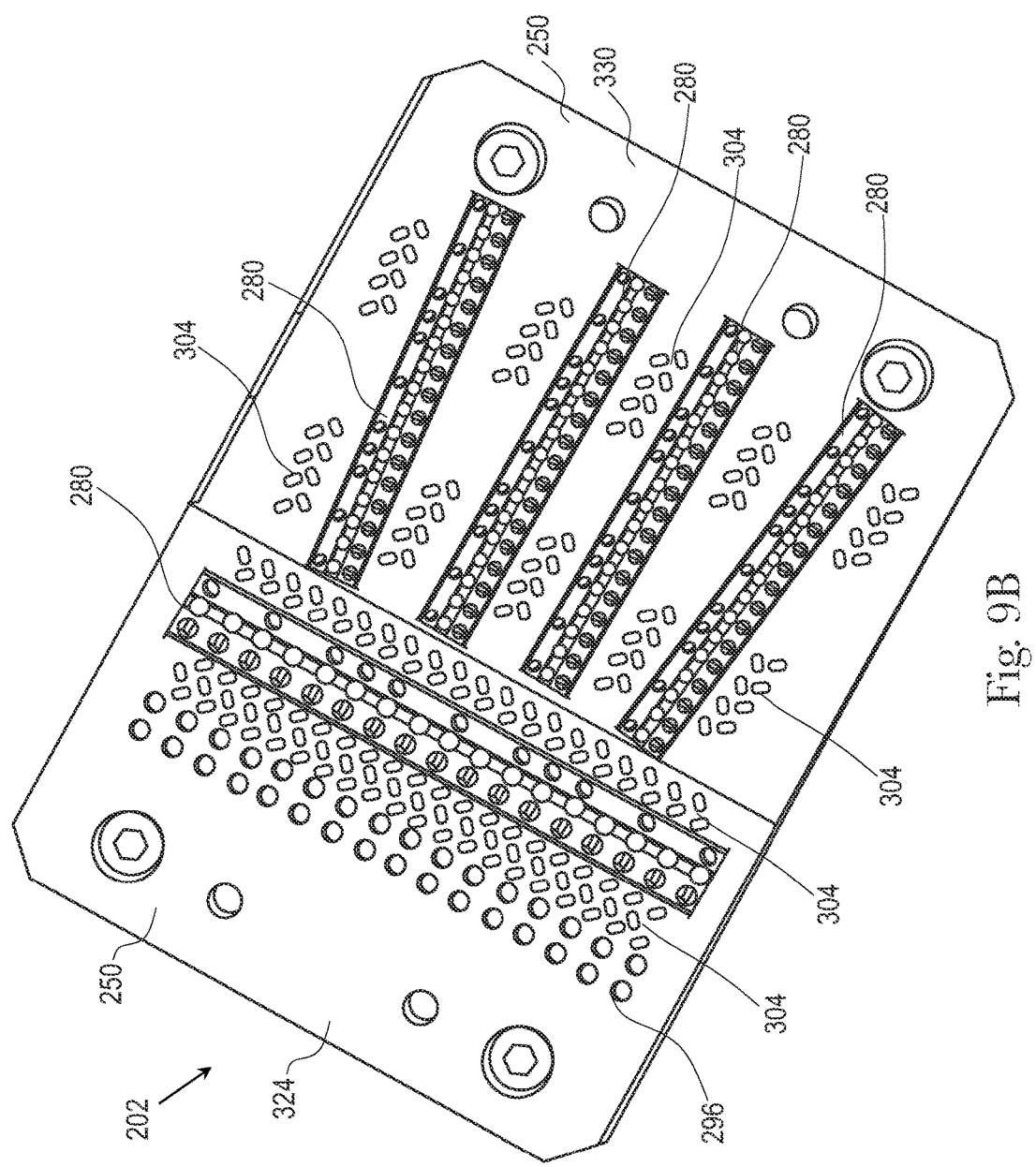
FIG. 9B is a perspective view of a folding member in accordance with one non-limiting embodiment of the present disclosure.

FIG. 9B illustrates another exemplary embodiment of the folding member 202. As shown in FIG. 9B, the folding member 202 may include one or more groove portions 280 and each grove portion may be positioned at some angle with respect to another groove portion 280. For example, one groove portion may be positioned substantially parallel to and/or substantially perpendicular to an adjacent groove portion. Further, each groove portion 280 may include a plurality of apertures, as previously discussed. Further still, in some embodiments, the folding member 202 may also include a number of bonding portions 304 positioned adjacent to the groove portions 280, as previously discussed. It is also to be appreciated that the folding member 202 may include any number of grooves, apertures, and bonding portions. The number of grooves, apertures, and bonding portions will depend on the number and position of rugosities to be present in the discrete substrate attached to another substrate.

Figure 10A:
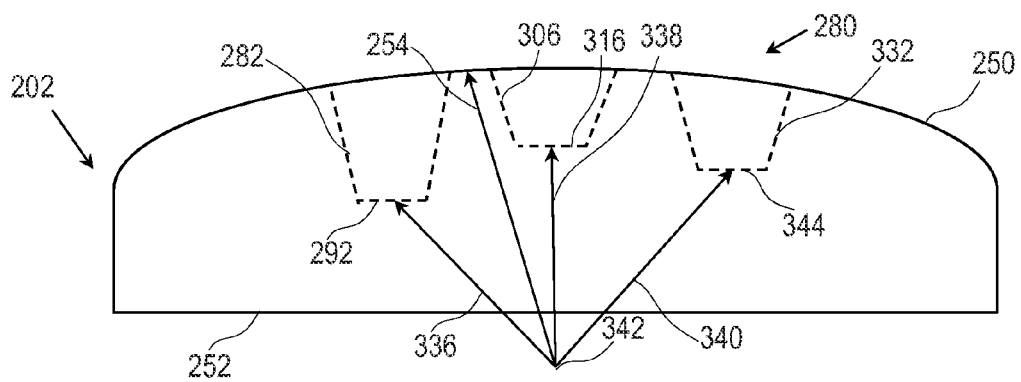
FIG. 10A is a side view of a folding member in accordance with one non-limiting embodiment of the present disclosure.
Figure 10B:
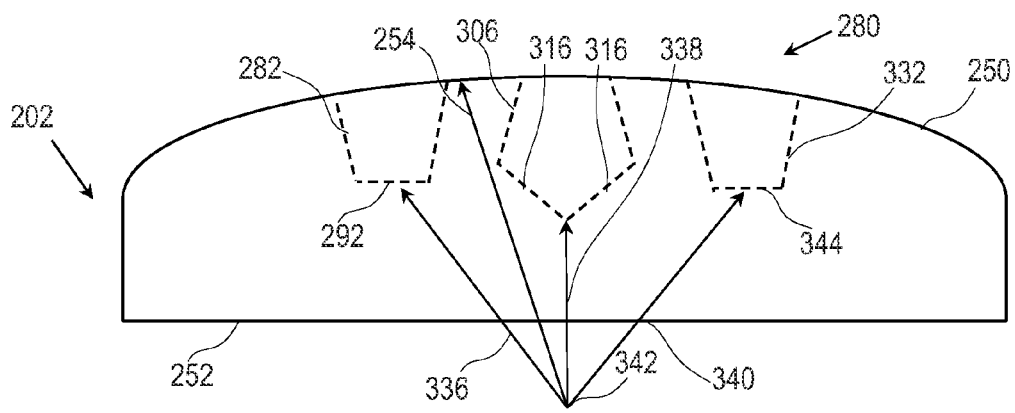
FIG. 10B is a side view of a folding member in accordance with one non-limiting embodiment of the present disclosure.
Figure 10C:
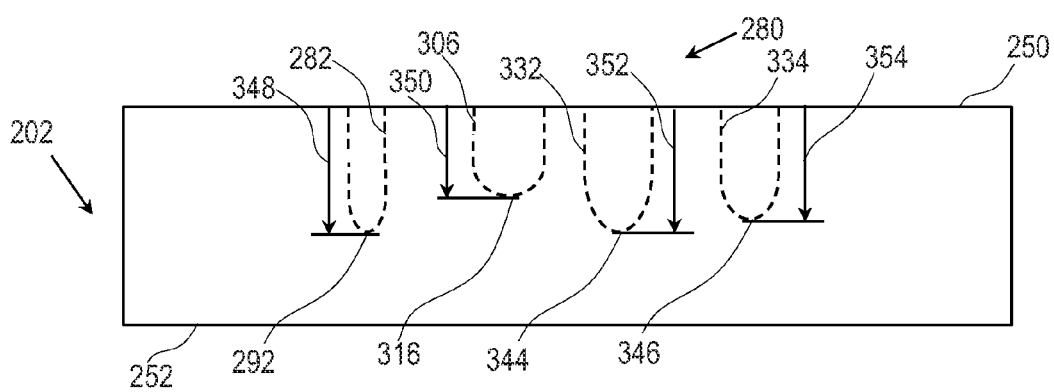
FIG. 10C is a side view of a folding member in accordance with one non-limiting embodiment of the present disclosure.

FIGS. 10A-10C illustrate a side view of a folding member 202 including a groove portion having a groove. The groove portion 280 may include a first groove 282, a second groove 306, a third groove 332, and/or a fourth groove 334. As previously discussed, the folding member 202 may include a first surface 250. The first surface 250 may have a first surface radius 254. The first surface radius 254 may be a predetermined radius that may be the same as or similar to the outer radius 226 of the folding roll 204. The first surface radius 254 may define a radius center 342. Further, the groove portion 280 may include one or more grooves, wherein each groove protrudes into the folding member 202 such that each groove may have a groove radius less than the first surface radius and/or a surface distance. The groove radius may be measured from the radius center 342 of the folding member as defined by the first surface radius 254 to the base portion of each groove. Similarly, in some embodiments, the folding member 202 may not include a first surface radius 254 because the first surface 250 may be substantially flat. In the embodiments that include a folding member 202 with a substantially flat first surface 250, the groove may include a surface distance that is greater than zero. The surface distance is the distance measured substantially perpendicularly from the first surface 250 of the folding member 202 to the base portion of the groove. It is to be appreciated that the folding member 202 may include a groove portion that includes any number of grooves. The number of grooves present may depend on the desired resulting profile of the discrete absorbent substrate.

In some exemplary embodiments, such as that shown in FIGS. 10A and 10B, the folding member 202 may include a first surface 250 having a first surface radius 254 and a groove portion 280. The groove portion 280 may include a first groove 282, a second groove 306, and a third groove 332. The first groove 282, the second groove 306, and the third groove 332 may include a first base portion 292, a second base portion 316, and a third base portion 344, respectively. The first groove portion 280 may include a first groove radius 336 that is measured from the radius center 342 to the base portion 292. Similarly, the second groove 306 may include a second groove radius 338 that is measured from the radius center 342 to the second base portion 316, and the third groove 332 may include a third groove radius 340 measured from the radius center 342 to the third base portion 344. Thus, each groove radius may be measured with respect to the first surface radius 254 and, more specifically, the radius center 342. Generally, the first groove radius 336, the second groove radius 338, and the third groove radius 340 may be less than the first surface radius 254. The first groove radius 336 may be less than, greater than, or equal to the second grove radius 338 and the third groove radius 340. The second groove radius 338 may be less than, greater than, or equal to the first groove radius 336 and the third groove radius 340. The third groove radius 340 may be less than, greater than, or equal to the first groove radius 336 and the second groove radius 338.

Referring to FIG. 10C, the folding member 202 may include a first surface 250 that is substantially flat, such that the first surface has no radius of curvature, and a groove portion 280. The groove portion 280 may include a first groove 282, a second groove 306, a third groove 332, and a fourth groove 334. The first groove 282, the second groove 306, the third groove 332, and the fourth groove 334 may include a first base portion 292, a second base portion 316, a third base portion 344, and a fourth base portion 346, respectively. The first groove 282 may include a first distance 348 that extends from the first surface to the first base portion 292. The second groove 306 may include a second distance 350 that extends from the first surface 250 to the second base portion 316. The third groove 332 may include a third distance 352 that extends from the first surface 250 to the third base portion 344. Further, the fourth groove 334 may include a fourth distance 354 that extends from the first surface 250 to the fourth base portion 346. Any one of the first distance 348, the second distance 350, the third distance 352, and the fourth distance 354 may be greater than, less than, or equal to each other. Generally, the first distance 348, the second distance 350, the third distance 352, and the fourth distance 354 may be a distance greater than zero measured perpendicularly from the first surface 250 toward the second surface 252.

Referring to FIGS. 10A-10C, it is to be appreciated that each groove may be any shape that aids in pulling the discrete substrate into the groove and forming the desired profile of the discrete substrate when attached to another substrate.

Figure 11:
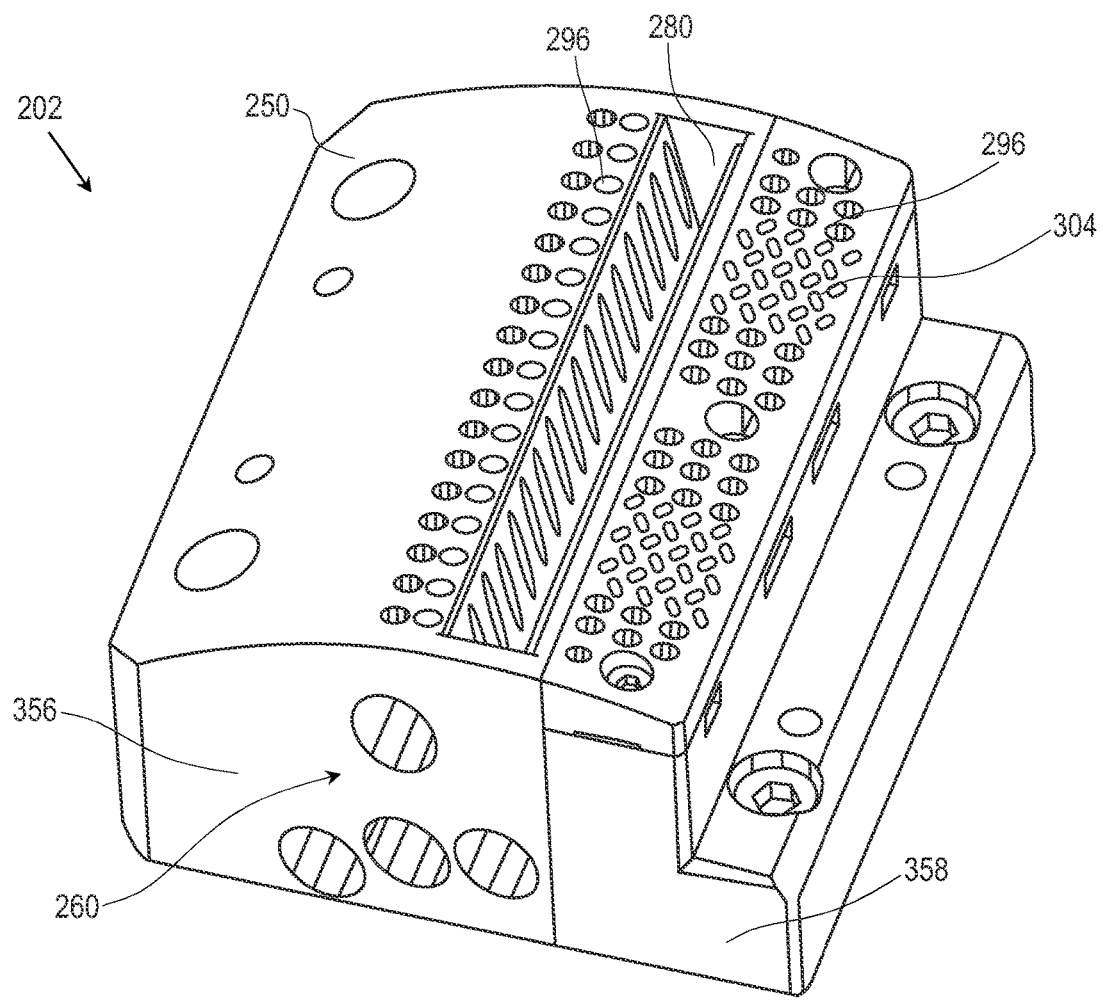
FIG. 11 is a perspective view of a folding member in accordance with one non-limiting embodiment of the present disclosure.

The folding member 202 may be a unitary structure, as illustrated in FIGS. 8 and 9, or the folding member 202 may include one or more segments as illustrated in FIG. 11. FIG. 11 illustrates a folding member 202 comprising a first segment 356 and a second segment 358. The folding member 202 may be broken up into one or more segments that may be attached to one another to facilitate quick and easy replacement of parts during the manufacturing process. In addition, it may be necessary to make different segments of the folding member 202 from different materials. For example, the first segment 356 may be made from a polymer and the second segment 358 may be made from metal. The segments may be attached mechanically and/or chemically. For example, the segments may be attached mechanically by screws or clamps and chemically by adhesives.

Figure 12:
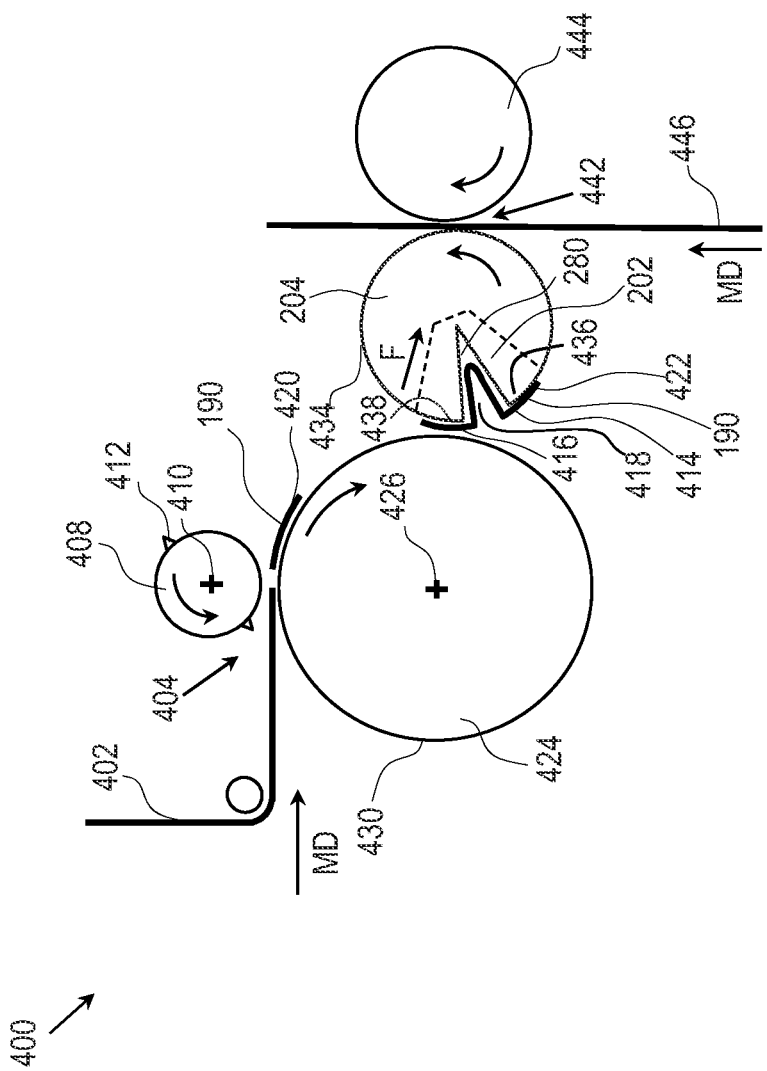
FIG. 12 is a schematic representation of a process used to manufacture a substrate including a discrete substrate having a rugosity in accordance with one non-limiting embodiment of the present disclosure.

The folding member 202 may be used in various processes to form a substrate that includes a discrete substrate including a rugosity. An exemplary process 400 is illustrated in FIG. 12. A first substrate 402 may be advanced toward a cut and slip device 404. The cut and slip device 404 may be used to cut the first substrate 402 to form a discrete substrate 190 and space each discrete substrate a certain distance away from each adjacent discrete substrate. Example operations/equipment for achieving the spacing between the discrete substrates are disclosed in U.S. Pat. No. 5,702,551, sometimes referred to as a cut and slip operation/device. Other types of operations and equipment that may be used to cut and space discrete components are disclosed in U.S. Pat. Nos. 6,450,321; 6,705,453; and EP 0 812 789 A2. In some example embodiments, the cut and slip device 244 may include a cutting roll 250 that operatively engages a slip roll 252. The cutting roll 250 may include a blade 246 that extends radially outward from the surface 248 of the cutting roll 408. The cutting roll 408 may rotate about a central axis 410 causing the blades 412 to rotate about the central axis 410. The blade 412 may engage the first substrate 402 separating a portion of the first substrate 402 to form a discrete substrate 190. The discrete substrate 190 may include a leading edge portion 414, a trailing edge portion 416 opposite the leading edge portion, and a central portion 418 between the leading edge portion 414 and the trailing edge portion 418. The discrete substrate 190 may also include a first surface 420 and a second surface 422 opposite the first surface 420. The discrete substrate 190 may be extensible in at least one of the machine direction and the cross direction.

The slip roll 424 may rotate about a central axis 426 to advance the discrete substrate 190 toward a folding roll 204, such as that illustrated in FIG. 5. More specifically, the second surface 422 of the discrete substrate 190 may be in facing relationship with the outer surface 430 of the slip roll 424. The discrete substrate 190 may advance in the machine direction MD about the central axis 426 of the slip roll 252 such that the leading edge portion 414 may be the first to associate with the folding roll 204.

Upon disassociating with the slip roll 424 the discrete substrate 190 may be folded. As illustrated in FIG. 12, the discrete substrate 190 may be transferred from the slip roll 424 to the folding roll 204. The folding roll 204 may include a folding member 202, such as that previously discuss with respect to FIGS. 8-11. It is to be appreciated that the folding member 202 may be formed as part of the folding roll 204 or independently from the folding roll 204 such that the folding member 202 is removably associated with the folding roll 204. Further, the folding roll 204 may be in fluid communication with a vacuum source (not shown) such that a vacuum force F may act on at least a portion of the discrete substrate 190. The vacuum force F may act on the discrete substrate 190 such that the first surface 420 associates with the outer surface 434 of the folding roll 204 and the discrete substrate 190 remains associated with the folding roll 204 during rotation. The leading edge portion 414 may associate with a first leading edge portion 436 of the folding roll 204 and/or the folding member 202. Similarly, the trailing edge portion 416 may associate with the trailing edge portion 438 of the folding roll 204 and/or the folding member 202. The central portion 418 of the discrete substrate 190 may associate with the groove portion 280 of the folding member 202. The vacuum force F may cause the central portion 418 of the discrete substrate 190 to associate with the groove portion 280 forming a fold in the discrete substrate 190. It is to be appreciated that the groove portion 280 may include any number of topographies, such as one or more grooves, that may be used to fold the discrete substrate. The discrete substrate 190 may be advanced toward a bonding area 442 and a second substrate 446. The second substrate 446, which may be a continuous substrate, may also be advanced in the machine direction MD toward the bonding area 442. The bonding area 442 may include a bond roll 444.

The leading edge portion 416 of the discrete substrate 190 may first associate with the second substrate 446 as the folding roll 204 rotates. The remainder of the discrete substrate 190 associates with the second substrate 446 as the folding roll 204 continues to rotate. Further, the second substrate 446 and the discrete substrate 190 may be advanced into the bonding area 442. In the bonding area 442, at least a portion of the discrete substrate 190 may be bonded to the second substrate 446. More specifically, for example, the trailing edge portion 416 and the leading edge portion 414 of the discrete substrate 190 may be connected to at least one of the first surface and the second surface of the second substrate 446, as illustrated in FIG. 13. The position of the bonds may depend on the desired final profile of the discrete substrate 190 on the second substrate 446.

The bond between the discrete substrate 190 and the second substrate 446 may be by, for example, high pressure welding, hot air welding, heat crimping, or ultrasonic welding. Exemplary bonding methods and apparatuses may include those described in U.S. Pat. Nos. 4,854,984; 4,919,738; 5,711,847; 5,817,199; 6,123,792; 7,449,084; 6,248,195; 6,546,987; and U.S. patent application Ser. Nos. 14/038,812; 61/836,690; and 61/836,745. The bond between the discrete substrate 190 and the second substrates 446 may also include the use of adhesives alone or in addition to the aforementioned types of bonding. However, it has been found that limiting the use of adhesives in absorbent articles, such as diapers, is desirable to consumers and manufacturers. For consumers, the desire for limited use or non-use of adhesives may be a result of, for example, actual or perceived irritation of the wearer's skin. For manufacturers, the desire for limited use of adhesive may be a result of numerous challenges in handling the adhesive during the manufacturing process. For example, adhesive often require a certain period of time to adhere and/or solidify, which may cause a delay in the manufacturing process. Although adhesives may be used in absorbent articles, the absorbent article including a discrete substrate of the present disclosure may be assembled without the use of adhesives.

FIG. 13 illustrates an example embodiment of a discrete substrate 190 including a rugosity 448 disposed on a second substrate 446 as produced by the aforementioned process. The discrete substrate 190 may be bonded to the second substrate 446 by a bond region 450. It is to be appreciated that the folding member 202 may be designed to produce a substrate including a discrete substrate 190 having a number of rugosities. The rugosities may be positioned parallel to one another and/or at an angle to one another. Further, the rugosities may be oriented in the machine direction and/or the cross direction.

In view of the aforementioned, a method for manufacturing a substrate including a discrete substrate with a rugosity may include the following steps. A folding roll, as shown in FIG. 5, may be provided. The folding roll may include a folding member and an outer circumferential surface extending between a first roll surface and a second roll surface. At least one of the first roll surface and the second roll surface may include an external vacuum portion. Further, the folding member, as shown in FIG. 8, may include a leading edge portion, a trailing edge portion opposite the leading edge portion, a groove portion between the leading edge portion and the trailing edge portion and a plurality of apertures disposed on at least one of the leading edge portion, the trailing edge portion, and the groove portion. The plurality of apertures may be fluidly connected to the external vacuum portion. A discrete substrate may be advanced in the machine direction MD. The discrete substrate may include a leading edge portion, a trailing edge portion opposite the leading edge portion, and a central portion between the leading edge portion and the trailing edge portion. The leading edge portion of the discrete substrate may associate with the leading portion of the folding member by activating a first vacuum port of the external vacuum portion. Further, the central portion of the discrete substrate may associate with the groove portion of the folding member by activating a second vacuum port of the external vacuum portion. Further still, the trailing portion of the discrete substrate may associate with the trailing portion of the folding member by activating a third vacuum port of the external vacuum portion. The first, second, and third vacuum port are activated sequentially. A second a substrate may be advanced in the machine direction MD. The second substrate may include a first substrate surface and a second substrate surface opposite the first substrate surface. The discrete substrate may be bonded to at least one of the first substrate surface and the second substrate surface. The discrete substrate bonded to the substrate forms a rugosity.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method for forming a substrate comprising a discrete substrate including a rugosity, the method comprising the steps of:
   providing a folding roll comprising a folding member and an outer circumferential surface extending between a first roll surface and a second roll surface, wherein at least one of the first roll surface and the second roll surface comprise an external vacuum portion, and wherein the folding member comprises a leading edge portion, a trailing edge portion opposite the leading edge portion, a groove portion between the leading edge portion and the trailing edge portion and a plurality of apertures disposed on at least one of the leading edge portion, the trailing edge portion, and the groove portion, and wherein the plurality of apertures are fluidly connected to the external vacuum portion;
   advancing a discrete substrate comprising a leading edge portion, a trailing edge portion opposite the leading edge portion, and a central portion between the leading edge portion and the trailing edge portion;

associating the leading edge portion of the discrete substrate with the leading edge portion of the folding member by activating a first vacuum port of the external vacuum portion;

associating the central portion of the discrete substrate with the groove portion of the folding member by activating a second vacuum port of the external vacuum portion, wherein the central portion folds down into the groove portion;

associating the trailing portion of the discrete substrate with the trailing portion of the folding member by activating a third vacuum port of the external vacuum portion;

advancing a substrate comprising a first substrate surface and a second substrate surface opposite the first substrate surface; and bonding the discrete substrate to at least one of the first substrate surface and the second substrate surface, wherein the discrete substrate bonded to the substrate forms a rugosity, wherein the groove portion is taken the same shape as the rugosity, and wherein the first, second, and third vacuum port are activated sequentially, wherein the folding member is removably associated with the folding roll.

2. The method of claim 1, wherein the groove portion comprises a first groove and a second groove adjacent to the first groove.

3. The method of claim 1, further comprising the step of rotating the folding roll about a central longitudinal roll axis.

4. The method of claim 1, wherein the folding member comprises a bonding portion.

* * * * *